(12) United States Patent
Jaeger, Jr. et al.

(10) Patent No.: US 12,216,445 B1
(45) Date of Patent: Feb. 4, 2025

(54) FLUID CONDITION SENSOR AND MAINTENANCE SYSTEMS AND METHODS

(71) Applicant: ESL TEKnologies LLC, Dallas, TX (US)

(72) Inventors: John Tiffany Jaeger, Jr., Dallas, TX (US); Jason Lamb, Dallas, TX (US)

(73) Assignee: ESL TEKnologies LLC, Dallas, TX (US)

( * ) Notice: Subject to any disclaimer, the term of this patent is extended or adjusted under 35 U.S.C. 154(b) by 304 days.

(21) Appl. No.: 17/732,455

(22) Filed: Apr. 28, 2022

Related U.S. Application Data (60) Provisional application No. 63/188,943, filed on May 14, 2021.

(51) Int. Cl.
| | | |
|---|---|---|
| *G05B 19/05* | (2006.01) | |
| *G01N 33/00* | (2006.01) | |
| *H04W 4/38* | (2018.01) | |
| *H04W 88/16* | (2009.01) | |

(52) U.S. Cl.
CPC .......... *G05B 19/058* (2013.01); *G01N 33/00* (2013.01); *H04W 4/38* (2018.02); *H04W 88/16* (2013.01)

(58) Field of Classification Search
USPC ............................................................ 702/1
See application file for complete search history.

(56) References Cited

U.S. PATENT DOCUMENTS

| | | | |
|---|---|---|---|
| 10,738,804 B2 | 8/2020 | Oehler et al. | |
| 2009/0115436 A1* | 5/2009 | Koehler, III | G01N 33/2829 324/698 |
| 2010/0102974 A1* | 4/2010 | Keast | F15B 19/005 340/626 |
| 2017/0002921 A1* | 1/2017 | Ture | F16H 57/0404 |
| 2017/0011298 A1* | 1/2017 | Pal | H04L 67/12 |
| 2017/0168034 A1* | 6/2017 | Fenton | G01K 13/02 |
| 2017/0307580 A1* | 10/2017 | Kim | G01N 27/08 |
| 2019/0323337 A1* | 10/2019 | Glass | E21B 47/008 |
| 2021/0231634 A1* | 7/2021 | Gillette | G01N 33/2847 |

* cited by examiner

*Primary Examiner* — Paul D Lee
(74) *Attorney, Agent, or Firm* — Fogarty LLP (57) ABSTRACT

An industrial internet of things (IoT) gateway is communicatively coupled to (a) fluid condition sensor(s) monitoring (an) operating parameter(s) of fluid power system fluid, via a programmable logic controller (PLC) data communications protocol interface. The IoT gateway includes a PLC data communications protocol interface master function, a cloud computing interface module and program instructions to periodically sample fluid condition sensor readings, format the readings, and send the readings to a cloud computing message queuing telemetry transport broker for processing by a cloud monitoring system. Machine learning provides predictions of fluid quality and buildup of varnish in the fluid system, applies a scoring algorithm to predict fluid system failure. These predictions may be used to automatically create (a) work ticket(s) related to the fluid system. Servicing by mitigation of varnish, installation of the sensor system, issuance of a warranty, guarantee and/or service contract, and/or financing thereof, may be provided.

20 Claims, 8 Drawing Sheets

FLUID CONDITION SENSOR AND MAINTENANCE SYSTEMS AND METHODS

CROSS-REFERENCE TO RELATED APPLICATION

This application claims benefit of U.S. Provisional Patent Application Ser. No. 63/188,943, entitled Fluid Condition Sensor Systems and Methods, filed May 14, 2021, which is incorporated herein by reference.

TECHNICAL FIELD

The present disclosure relates generally to fluid systems, more particularly to fluid power systems, and specifically to embodiments of fluid condition sensor and maintenance systems and methods.

BACKGROUND

As used herein the term "fluid power" includes the use of a fluid under pressure to generate, control, and transmit power, provide lubrication, and/or the like. For example, fluid power system may include hydraulic systems, such as may be used to power hydraulic elevator systems, airport jetways, and the like, and lubrication systems, such as may be employed by internal combustion engines, turbines for lubrication of turbine bearings and to provide a seal around the shaft between the steam or hot gas on the turbine side and the power generation side, or the like.

Many fluid power systems receive no planned maintenance and/or inspection services. That is, there is little, or no, awareness of the importance of fluid quality, much less real time visibility into the operational condition. For example, there may be no provisions to change out fluids. Such fluids may only be topped off when performance of the fluid power system degrades, and low-quality fluids may be used to do so. This may result in increase in presence of sludge in the fluid and/or varnish buildup on component parts, which may lead to high repair, replacement, and labor costs, increase safety incidents, increased liability coverage expenditures, tarnished brand image due to user experiences, and/or the like. "Varnish" is a wide-ranging term encompassing various types of deposits in oil systems. Some types are hard and tenacious, others sticky, and still others soft and thick, commonly referred to as sludge. What they have in common is they typically originate from the breakdown or degradation of the oil in the system. Varnish usually forms and sticks in areas that are either very hot or very cool and stagnant. Varnish contamination may typically be a byproduct of degradation processes in hydraulic and lubrication systems. For example, oxidation may result from thermal stressing of hydraulic oil, and the byproducts of oxidation may overcome the solubility of the oil and can lead to the formation of varnish in hydraulic control and lubricating oil systems. Varnish buildup in fluid power system control valves, or the like is particularly problematic.

Legacy methods to track and attempt to improve fluid power system safety are manual in nature, largely relying on a reactive approach of tackling issues based on incidents reported, or the like. For example, an executive, who might oversee operations across multiple properties may typically find it difficult to get a holistic view of safety across properties, have no real-time proactive benchmark to measure and compare property safety and lack insights and recommendations for improving property safety. As a further example, a property manager, who, for example, oversees all operations of a property, or the like, may find it difficult to track and monitor fluid power system status in real-time, typically is not provided smart insights to proactively enhance safety and may be provided disparate systems informing different safety measures, or the like.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The present invention is directed to systems and methods which provide fluid condition sensing and maintenance. Therein a fluid condition sensor system may include one or more fluid condition sensors configured to monitor one or more operating parameters of fluid in a fluid power system and an industrial internet of things (IoT) gateway, or the like, communicatively coupled to the fluid condition sensor(s) for communication of the operating parameter(s) of the fluid in the fluid power system, via a programmable logic controller (PLC) data communications protocol interface, or the like. The industrial IoT gateway may include a PLC data communications protocol interface master function, a cloud computing interface module, program instructions, and/or the like. The program instructions, when executed by the industrial IoT gateway, may cause the industrial IoT gateway to periodically sample fluid condition sensor readings via the PLC data communications protocol interface, format the readings, and send the readings to a cloud computing message queuing telemetry transport broker for processing by a cloud monitoring system. These program instructions may include machine learning, or the like, employed to provide predictions of fluid quality, which, in some implementations, may be used by the program instructions to create a work ticket related to the fluid power system. The machine learning may additionally, or alternatively, be employed to provide predictions of buildup of varnish in the fluid power system, which, in some implementations, may (also) be used by the program instructions to create a work ticket related to the fluid power system.

Additionally, or alternatively, a scoring algorithm may apply machine learning to predict fluid power system failure. In such implementations, the PLC data communications protocol interface may poll the connected one or more sensors at a frequency that increases as indication of non-nominal sensor readings are received, and the program instructions may further develop trend data to provide predictive analytics, therefrom. Preemptive alerts may be provided, via text messages, emails, an application program interface of a third-party system, on a user interface of the cloud monitoring system, and/or likewise, of the predictions of fluid quality, buildup of varnish in the fluid power system and/or fluid power system failure.

Thus, a fluid condition sensor process may include monitoring, by fluid condition sensor(s), one or more parameter(s) of fluid in a fluid power system and communicating the one or more parameter(s) of the fluid in the fluid power system to an industrial IoT gateway, or the like, via a PLC data communications protocol interface, or the like. Therein, the industrial IoT gateway, or the like may employ a PLC data communications protocol interface master function, a cloud computing interface module, program instructions and or the like, to periodically sample fluid condition sensor readings, such as, via the PLC data communications protocol interface, format these readings, and send the (formatted) readings to a cloud computing message queuing telemetry transport broker for processing by a cloud monitoring system. Machine learning may provide predictions of fluid quality, buildup of varnish in the fluid power system, and/or the like, and such predictions may be used to create (a) work ticket(s) related to the fluid power system. A scoring algorithm may apply machine learning to predict fluid power system failure and the PLC data communications protocol interface, or the like may poll the sensor(s) at a frequency that increases as indication of non-nominal sensor readings are received. Trend data may be developed, therefrom, to provide predictive analytics, and preemptive alerts may be provided, via text messages, emails, an application program interface of a third-party system, on a user interface of the cloud monitoring system, and/or the like of the predictions of fluid quality, buildup of varnish in the fluid power system and/or fluid power system failure.

In accordance with the foregoing, servicing for a fluid power system may include mitigating (i.e., cleaning) varnish off of surfaces in the fluid power system, installation of the fluid condition sensor system having the fluid condition sensor(s) monitoring operating parameter(s) of fluid in the fluid power system and the industrial IoT gateway communicatively coupled to the fluid condition sensor(s). As described, the industrial IoT gateway may include a PLC data communications protocol interface master function, a cloud computing interface module, and/or the like. Also, as described, the industrial IoT gateway may periodically sample fluid condition sensor readings via the PLC data communications protocol interface, format the readings, and send the readings to a cloud computing message queuing telemetry transport broker for processing by a cloud monitoring system. Further, in accordance with such servicing of the fluid power system, a warranty, guarantee and/or service contract covering repair and/or replacement of named components that breakdown due to failure of the fluid power system may be issued, or otherwise obtained. The cloud monitoring system, or the like may provide monitoring of the operating parameter(s) of fluid in the fluid power system, and machine learning may provide predictions of fluid quality, predictions of buildup of varnish in the fluid power system, and/or the like. Additionally, or alternatively, a scoring algorithm, and/or the like, may apply machine learning to predict fluid power system failure. The predictions of fluid quality, the predictions of buildup of varnish in the fluid power system, a prediction of fluid power system failure, and/or the like may be used to create (a) work ticket(s) related to the fluid power system.

Further, as described above, such a servicing process may use the PLC data communications protocol interface, or the like, to poll the connected sensor(s), at a frequency that increases as indication of non-nominal sensor readings are received, and may develop trend data to provide predictive analytics therefrom. Also, under the servicing process, preemptive alerts may be provided, via text messages, emails, an application program interface of a third-party system, on a user interface of the cloud monitoring system, and/or the like, of the predictions of fluid quality, buildup of varnish in the fluid power system and/or fluid power system failure.

Provisioning of the servicing process may be further facilitated by financing of the cleaning varnish off of surfaces in the fluid power system, installing the fluid condition sensor system, issuing or obtaining the warranty, guarantee and/or service contract, monitoring of the one or more operating parameters of fluid in the fluid power system, providing predictions of fluid quality and varnish in the fluid power system and/or predicting fluid power system failure.

In various embodiments, one or more of the techniques described herein may be performed by one or more computer systems. In other various embodiments, a tangible computer-readable storage medium may have program instructions stored thereon that, upon execution by one or more computer systems, cause the one or more computer systems to execute one or more operations disclosed herein. In yet other various embodiments, one or more systems may each include at least one processor and memory coupled to the processor(s), wherein the memory is configured to store program instructions executable by the processor(s) to cause the system(s) to execute one or more operations disclosed herein.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

Having thus described the invention in general terms, reference will now be made to the accompanying drawings, which are not necessarily drawn to scale, and wherein:

While this specification provides several embodiments and illustrative drawings, a person of ordinary skill in the art will recognize that the present specification is not limited only to the embodiments or drawings described. It should be understood that the drawings and detailed description are not intended to limit the specification to the particular form disclosed, but, on the contrary, the intention is to cover all modifications, equivalents and alternatives falling within the spirit and scope of the claims. Also, any headings used herein are for organizational purposes only and are not intended to limit the scope of the description. As used herein, the word "may" is meant to convey a permissive sense (i.e., meaning "having the potential to"), rather than a mandatory sense (i.e., meaning "must"). Similarly, the words "include," "including," and "includes" mean "including, but not limited to."

DETAILED DESCRIPTION

The invention now will be described more fully hereinafter with reference to the accompanying drawings. This invention may, however, be embodied in many different forms and should not be construed as limited to the embodiments set forth herein. Rather, these embodiments are provided so that this disclosure will be thorough and complete, and will fully convey the scope of the invention to those skilled in the art. One skilled in the art may be able to use the various embodiments of the invention.

Embodiments of the present systems and methods are directed to fluid systems, more particularly to fluid power systems, and specifically to embodiments of fluid condition sensor and maintenance systems and methods. As noted, as used herein the term "fluid power" includes the use of a fluid under pressure to generate, control, and transmit power, provide lubrication, and/or the like. For example, fluid power system may include hydraulic systems, such as may be used to power hydraulic elevator systems, airport jetways, and the like, and lubrication systems, such as may be employed by internal combustion engines, turbines for lubrication of turbine bearings and to provide a seal around the shaft between the steam or hot gas on the turbine side and the power generation side, or the like.

Embodiments of the present systems and methods provide twenty-four hour a day, seven days a week monitoring of sensor fluid for quality, fluid quality alerts and global visibility into all monitored fluid power systems, which, in conjunction with remediation of varnish and installation of state-of-the-art antioxidant fluid, address the above issues. The present systems and methods provide an improved metric to measure fluid power system safety through implementation of a unified platform to track all aspects of fluid power system performance, employing extensible algorithms that can, for example, be applied to other aspects of user safety.

Embodiments of the present fluid sensor systems and methods employ components linked as described below for logging sensor readings to a cloud monitoring system. The present systems and methods enable twenty-four hour a day, seven days a week, monitoring of sensor fluid quality for the identification of specific chemical composition and real-time alerting and monitoring (i.e., visibility). Embodiments of the present fluid sensor systems and methods provide an ability to integrate with a variety of available fluid sensors, across various industries. The present fluid sensor system and method architectures enable real time monitoring and scalability that does not currently exist in the fluid power industry.

In accordance with embodiments of the present systems and methods, as detailed below, an industrial internet of things (IoT) gateway is communicatively coupled to (a) fluid condition sensor(s) monitoring (an) operating parameter(s) of fluid power system fluid, via a programmable logic controller (PLC) data communications protocol interface. The IoT gateway includes a PLC data communications protocol interface master function, a cloud computing interface module and program instructions to periodically sample fluid condition sensor readings, format the readings, and send the readings to a cloud computing message queuing telemetry transport broker for processing by a cloud monitoring system. Machine learning provides predictions of fluid quality and buildup of varnish in the fluid system, applies a scoring algorithm to predict fluid system failure. These predictions may be used to automatically create (a) work ticket(s) related to the fluid system. Servicing by mitigation of varnish, installation of the sensor system and issuance of a warranty, guarantee and/or service contract, and/or financing thereof, may be provided.

Figure 1:
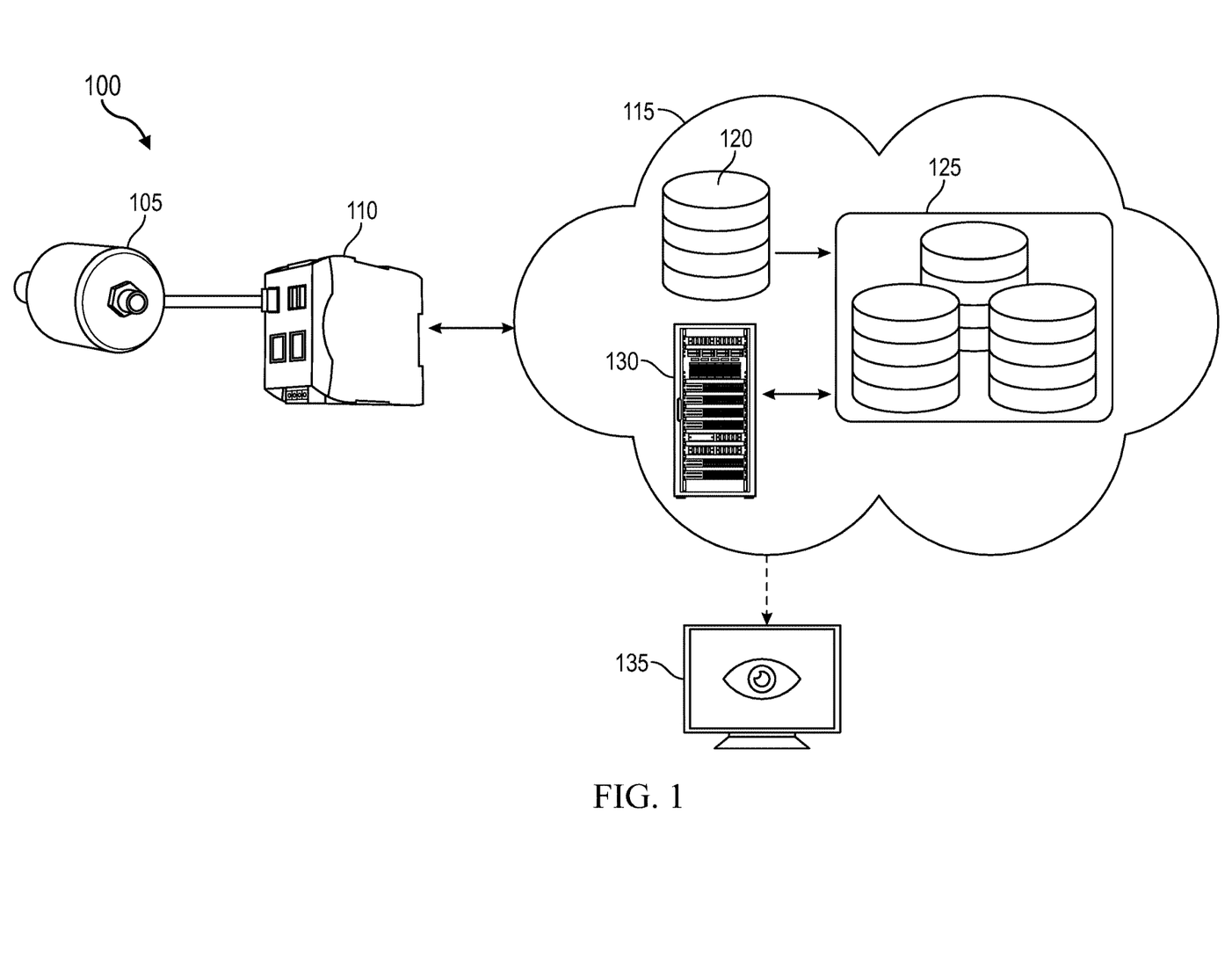
FIG. 1 is a block diagram of an example embodiment of the present fluid condition sensor system, according to some embodiments.

FIG. 1 is a block diagram of example fluid condition sensor system 100, according to some embodiments. Fluid condition sensor system 100 includes one or more fluid condition sensors 105 configured to monitor one or more operating parameters of fluid in a fluid power system. For example, fluid sensor system 100 may comprise one or more fluid condition sensors 105, such as, by way of example a PARKER KITTIWAKE™ fluid condition sensor from the "FCS31xx" fluid condition sensor family, or the like.

Industrial IoT gateway 110, or the like, is, in accordance with embodiments of the present systems and methods, communicatively coupled to fluid condition sensor(s) 105 for communication of the one or more operating parameters of the fluid in the fluid power system, via a PLC data communications protocol interface. Industrial IoT gateway 110 may be, such as by way of example, a single-board computer (e.g., Raspberry Pi) based industrial IoT gateway, a specific example of which may be a Kunbus Revolution Pi Connect+ Modbus Gateway, or the like. A power supply (not shown) may be associated with the IoT gateway, such as, by way of a specific example, a Meanwell™ MDR-60-24 60 watt DIN rail power supply, or the like, such as may be mounted in a DIN rail, or the like (not shown), a specific example of which may be a T&G™ DS357.5A11-203 8" DIN rail, or the like. Various embodiments of the present fluid sensor systems and methods may also make use of miscellaneous cables, (a) keyboard(s), (a) mouse(s), (a) monitor(s), and or the like, which may be communicatively coupled to industrial IoT gateway 110, or the like. Further Fluid condition sensor(s) 105 monitors one or more operating parameters of fluid in a fluid power system. Industrial IoT gateway 110 is communicatively coupled to the fluid condition sensor(s) for communication of the one or more operating parameters of the fluid in the fluid power system, via a PLC data communications protocol interface, such as a Modbus interface, which is associated with, or a part of IoT gateway 110.

Industrial IoT gateway 110 may include a PLC data communications protocol interface master function, a cloud computing interface module, and program instructions stored therein. The program instructions, when executed by industrial IoT gateway 110, may cause the industrial IoT gateway to periodically sample fluid condition sensor readings via the PLC data communications protocol interface, format the readings, and send the readings to the cloud 115. For example, industrial IoT gateway 110, may, in accordance with various embodiments of the present systems and methods, employ a Modbus master function, or the like, a cloud computing interface module (e.g., an Amazon™ Web Services (AWS™) IoT interface module), or the like, and programing (e.g., Python script, or the like). This programing may periodically sample fluid condition sensor readings via Modbus, format those readings, and send resulting readings 120 to cloud computing message queuing telemetry transport broker (e.g., big data repository 125) for processing by cloud monitoring system 130 of the present systems and methods.

In various embodiments, aspects of systems and methods described herein may be implemented, at least in part, using machine learning (ML). As used herein, the terms "machine learning" or "ML" refer to one or more algorithms that implement: a neural network (e.g., artificial neural network, deep neural network, convolutional neural network, recurrent neural network, autoencoders, reinforcement learning, etc.), fuzzy logic, artificial intelligence (AI), deep learning, deep structured learning hierarchical learning, support vector machine (SVM) (e.g., linear SVM, nonlinear SVM, SVM regression, etc.), decision tree learning (e.g., classification and regression tree or "CART"), Very Fast Decision Tree (VFDT), ensemble methods (e.g., ensemble learning, Random Forests, Bagging and Pasting, Patches and Subspaces, Boosting, Stacking, etc.), dimensionality reduction (e.g., Projection, Manifold Learning, Principal Components Analysis, etc.), or the like.

Non-limiting examples of publicly available machine learning algorithms, software, and libraries that may be utilized within embodiments of systems and methods described herein include, but are not limited to: PYTHON, OPENCV, INCEPTION, THEANO, TORCH, PYTORCH, PYLEARN2, NUMPY, BLOCKS, TENSORFLOW, MXNET, CAFFE, LASAGNE, KERAS, CHAINER, MATLAB Deep Learning, CNTK, MatConvNet (a MATLAB toolbox implementing convolutional neural networks for computer vision applications), DeepLearnToolbox (a Matlab toolbox for Deep Learning from Rasmus Berg Palm), BigDL, Cuda-Convnet (a fast C++/CUDA implementation of convolutional or feed-forward neural networks), Deep Belief Networks, RNNLM, RNNLIB-RNNLIB, matrbm, deeplearning4j, Eblearn.lsh, deepmat, MShadow, Matplotlib, SciPy, CXXNET, Nengo-Nengo, Eblearn, cudamat, Gnumpy, 3-way factored RBM and mcRBM, mPOT, ConvNet, ELEKTRONN, OpenNN, NEURALDESIGNER, Theano Generalized Hebbian Learning, Apache SINGA, Lightnet, and SimpleDNN.

The present systems and methods employ machine learning to provide predictions of fluid quality, which may be used to drive ticket creation (e.g., a fluid change or physical inspection order, or the like) based on established rules. The industrial IoT gateway program instructions include machine learning employed to provide predictions of fluid quality, predictions of buildup of varnish in the fluid power system, and/or the like. For example, varnish is identified by a real time polling mechanism that retrieves readings from the sensor(s) 105 and a data model employed by industrial IoT gateway 110 determines the level of varnish detected and the industrial IoT gateway provides the appropriate risk level based on the detected varnish level through cloud platform 130. Such predictions of fluid quality, predictions of buildup of varnish in the fluid power system, and/or the like, may be used by the industrial IoT gateway program instructions to create a work ticket, or the like, related to the fluid power system. Monitoring system 130, industrial IoT gateway 110, or the like, may, in accordance with various embodiments of the present systems and methods, include program instructions that employ a scoring algorithm, or the like, that applies machine learning to predict failure of the fluid power system.

Embodiments of the present systems and methods may employ any number of sensors in each fluid power system and poll the sensor in millisecond intervals for communication, through the PLC data communications protocol interface (Modbus), to the cloud. The present systems and methods may also employ a scoring algorithm that applies the aforementioned machine learning to predict fluid power system failure and provide preemptive alerts, via text messages, emails, an application program interface to a third-party system such as a building management company, assurance company, or the like, as well on a user interface.

Industrial IoT gateway 110's PLC data communications protocol interface (Modbus) may poll connected sensor(s) 105 at a frequency that increases as (an) indication(s) of non-nominal sensor readings are received to develop trend data for purposes of providing predictive analytics. Thus, the present systems and methods not only leverages each sensor's ability to detect physical properties of the fluid to provide chemical analysis of the fluid, but also scores data such as moisture, pressure, temperature, conductivity (metal particle content), and the like, to provide the aforementioned predictive modeling and resulting alerts.

Thereby, embodiments of the present systems and methods provide consistent sensor readings which may be varied in frequency, over time for transmission to the cloud and a user dashboard, such as may initiate at sensory data being read every second and visible on the dashboard to provide not only a snapshot or real-time sensor reading, but also any trending of the reading, as determined in accordance with the present systems and methods, as to provide the above discussed predictive models, which by way of example can communicate a condition such as a risk of failure in a particular frame of time (e.g., "x days"). For example, the industrial IoT gateway program instructions may provide preemptive alerts, via text messages, emails, an application program interface of a third-party system, and/or on user interface 135 of cloud monitoring system 130, or the like, of the predictions of fluid quality, buildup of varnish in the fluid power system, prediction(s) of fluid power system failure, and/or the like. in accordance with embodiments of the present systems and methods.

Figure 2:
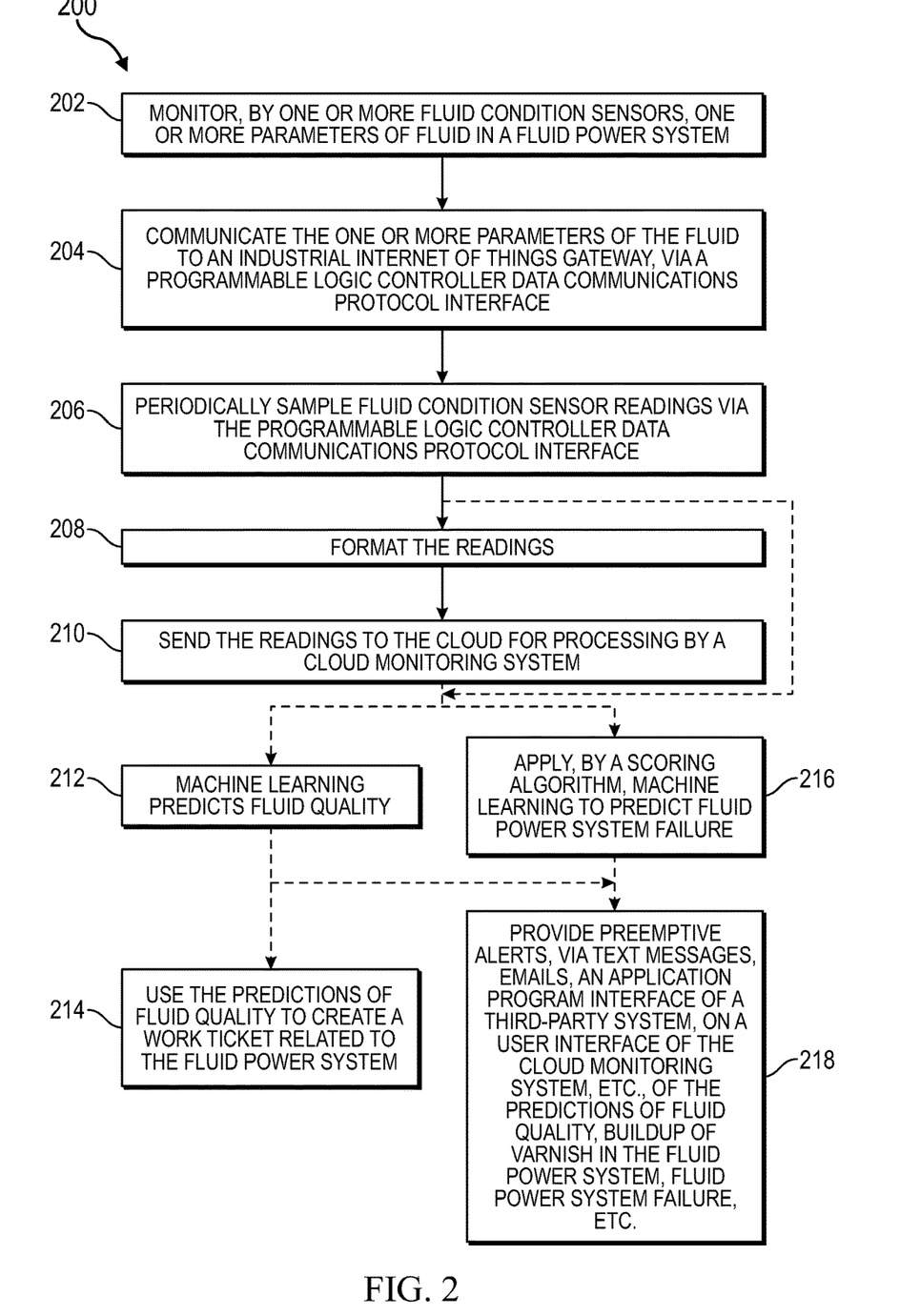
FIG. 2 is a flowchart of an example process for fluid condition sensing, according to some embodiments.

FIG. 2 is a flowchart of example fluid condition sensing process 200, according to some embodiments. Therein, at 202, one or more fluid condition sensors (105), monitor one or more parameters of fluid in a fluid power system, such as, by way of example fluid moisture content, temperature, pressure, conductivity (metal particle content), relative permittivity, etc. At 204 the parameter(s) of the fluid in the fluid power system are communicated to an industrial IoT gateway (110), via a PLC data communications protocol interface (of the IoT gateway). The industrial IoT gateway employs a PLC data communications protocol interface master function, a cloud computing interface module, and program instructions to, at 206, periodically sample fluid condition sensor readings, via the PLC data communications protocol interface, formatting these readings at 208, and at 210 send the formatted readings (120) to a cloud computing message queuing telemetry transport broker (125) for processing by a cloud monitoring system (130).

The IoT gateway program instructions may include machine learning, that at 212 provides predictions of fluid quality, predictions of buildup of varnish, and/or the like. For example, prediction of buildup of varnish may be accomplished by polling real time readings from the sensor and a deterministic model for predicting a rate of change in sensor readings based on historical readings and a predictive data model made from trend analytics. At 214 the IoT gateway program instructions may use these predictions of fluid quality, predictions of buildup of varnish, and/or the like, to create a work ticket related to the fluid power system. Additionally, or alternatively, a scoring algorithm may, at 216 apply machine learning to predict fluid power system failure. This may include polling, by the PLC data communications protocol interface, the connected sensor(s) (105) at a frequency that increases as indication of non-nominal sensor readings are received. Further in this regard, the program instructions may develop trend data to provide the aforementioned predictive analytics using the collected data. Such predictive analytics leverage sensor readings over time to generate trend analytics data are then feed into a predictive data model, or the like. Predictive data models leverage the trend and/or historical readings and/or data to proactively determine a future state of varnish levels, or the like. At 218, preemptive alerts may be provided, via text messages, emails, an application program interface of a third-party system, and/or on a user interface of the cloud monitoring system, of predictions of fluid quality, buildup of varnish in the fluid power system, fluid power system failure, and/or the like, so derived.

In accordance with the foregoing, embodiments of the present systems and methods provide continuous monitoring to an unlimited audience.

Figure 3:
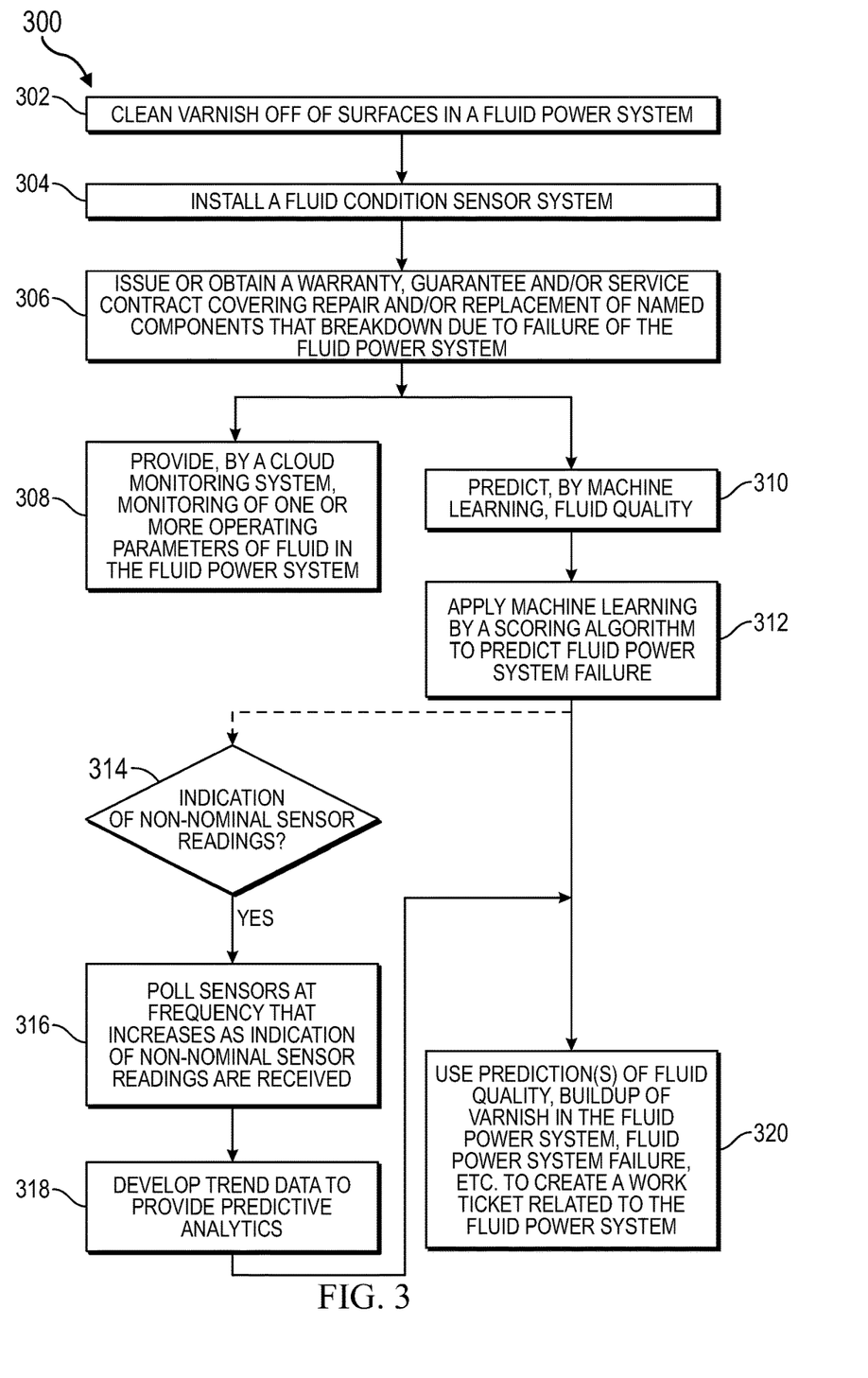
FIG. 3 is a flowchart of an example process for providing servicing for a fluid power system, according to some embodiments.

FIG. 3 is a flowchart of example process 300 for providing servicing for a fluid power system, according to some embodiments. Therein, at 302 varnish buildup in the fluid power system is mitigated by cleaning varnish off of surfaces in the fluid power system. This varnish mitigation may include, by way of example, flushing a hydraulic fluid circuit using a loop to the fluid circuit that includes a media filter, a micro-glass filter, and/or the like, in parallel to the fluid circuit, introducing a solvent cleaner into fluid, and maintaining the fluid at an elevated temperature. At 304, a fluid condition sensor system (100), is installed with respect to the fluid power system. As detailed above the fluid condition sensor system may include one or more fluid condition sensors (105) monitoring one or more operating parameters of fluid in the fluid power system, and an industrial IoT gateway (110) communicatively coupled to the fluid condition sensor(s). As also noted, the industrial IoT gateway communicates the operating parameter(s) of the fluid in the fluid power system, via a PLC data communications protocol interface, and to such ends, the industrial IoT gateway includes a PLC data communications protocol interface master function, a cloud computing interface module, and program instructions. These program instruction, as noted, cause the industrial IoT gateway to periodically sample fluid condition sensor readings via the PLC data communications protocol interface, format the readings, and send the formatted readings (120) to a cloud computing message queuing telemetry transport broker (125), or the like, for processing by a cloud monitoring system (130).

Process 300 further includes providing, at 306, a varnish-free warranty, guarantee or service contract covering the repair or replacement of named components that breakdown due to the failure of the fluid power system. For example, underwriting may be provided or obtained for such a warranty, guarantee or service contract against failure of the fluid power system, such as to provide repair or replacement of components damaged as a result of such failure. At 308, the cloud monitoring system may provide monitoring of the one or more operating parameters of fluid in the fluid power system. As noted, embodiments of the present systems and methods provide continuous monitoring to an unlimited audience. Additionally, or alternatively, preemptive alerts, may be provided via text messages, emails, an application program interface of a third-party system, and/or on a user interface (135) of the cloud monitoring system, of the predictions of fluid quality, buildup of varnish in the fluid power system, fluid power system failure, or the like.

At 310, machine learning in the IoT gateway program instructions provides predictions of fluid quality, predictions of buildup of varnish in the fluid power system, and/or the like, as detailed above, and at 312 a scoring algorithm applies machine learning to predict fluid power system failure. Additionally, such as detailed above, the IoT gateway PLC data communications protocol interface, or the like, may in response to a determination at 314 of (an) indication(s) of non-nominal sensor readings being received, poll the connected sensor(s) at 316 at an increased frequency that may increase based on further received indication(s) of non-nominal sensor readings. The IoT gateway program instructions may develop trend data to provide predictive analytics, therefrom, at 318. At 320, the IoT gateway program instructions may use the predictions of fluid quality, predictions of buildup of varnish in the fluid power system, a prediction of fluid power system failure, the predictive analytics, and/or the like, from 310, 312, 318, and/or the like, to create a work ticket related to the fluid power system, as necessary, such as for changing the fluid in the fluid power system, repeating mitigation of varnish in the fluid power system, replacement of fluid power system parts, and/or the like.

As a result of process 300, the fluid power system will protect the owner or operator of the elevator, airport jetway, turbine, or other system, from break downs due to varnish, if the fluid power system fails and as a result of that failure one or more of the named components, including, but not limited to, by way of example, (an) actuator(s), cylinder(s), motor(s) and/or pump(s) fails due to varnish, then the warranty, guarantee or service contract will cover the cost to repair or replace such components(s).

Various implementations of embodiments of the present systems and methods may employ financing of the service embodied in process 300, such as, as an additional component of service process 300. Financing may be offered as part of process 300, to finance mitigation of varnish at 302, purchase and/or installation of (a) sensor(s), (an) IoT gateway(s) and related equipment at 304, purchase of the warranty, guarantee or service contract at 306, and/or the continual, monitoring, analytic, cloud computing and alert services offered under 308 through 320, and/or the like. Thereby, customer cost for the service(s) under process 300 may be reduced to a monthly and affordable fee.

Figure 4:
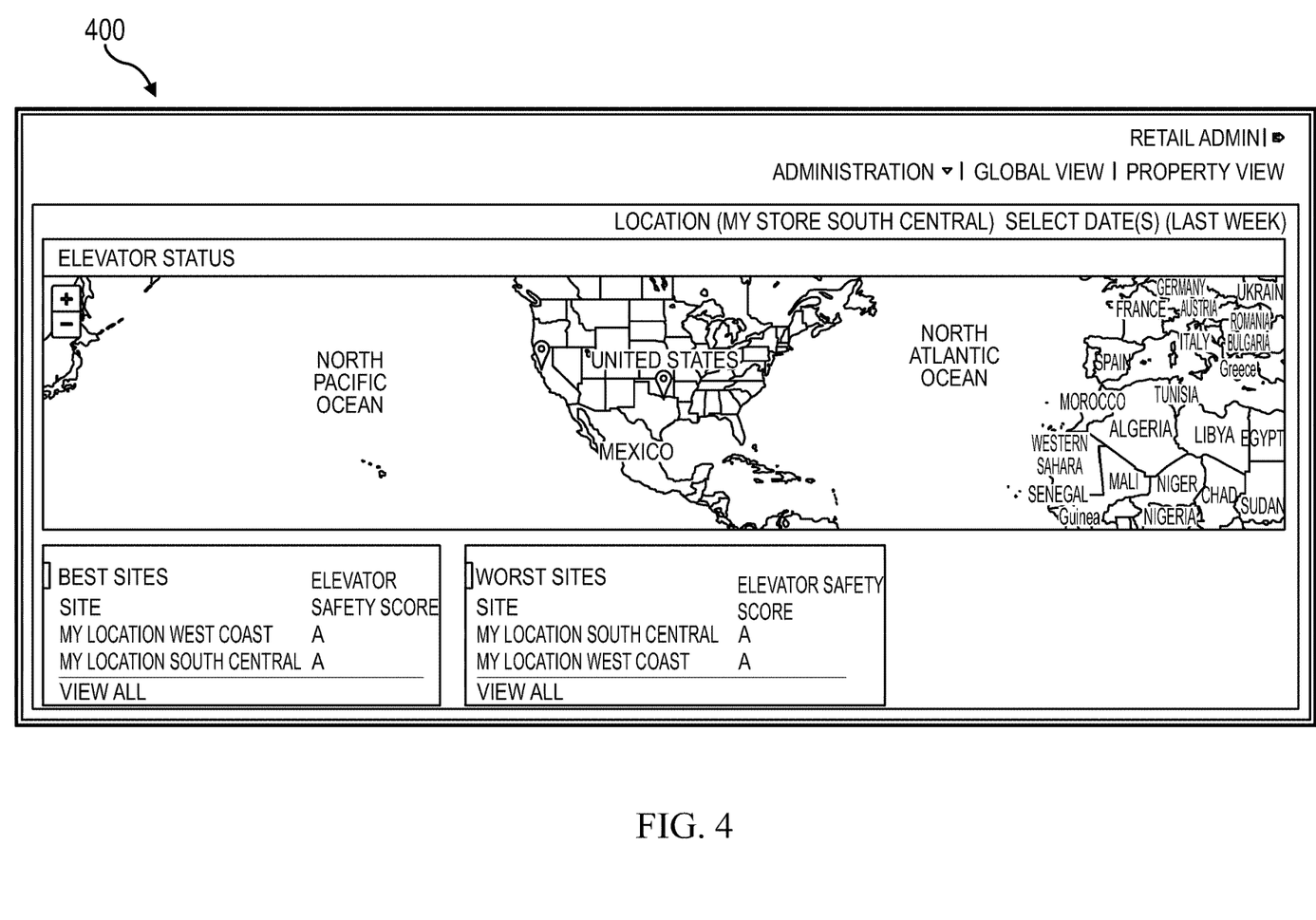
FIG. 4 is an illustration of a global fluid power system dashboard, according to some embodiments.
Figure 5:
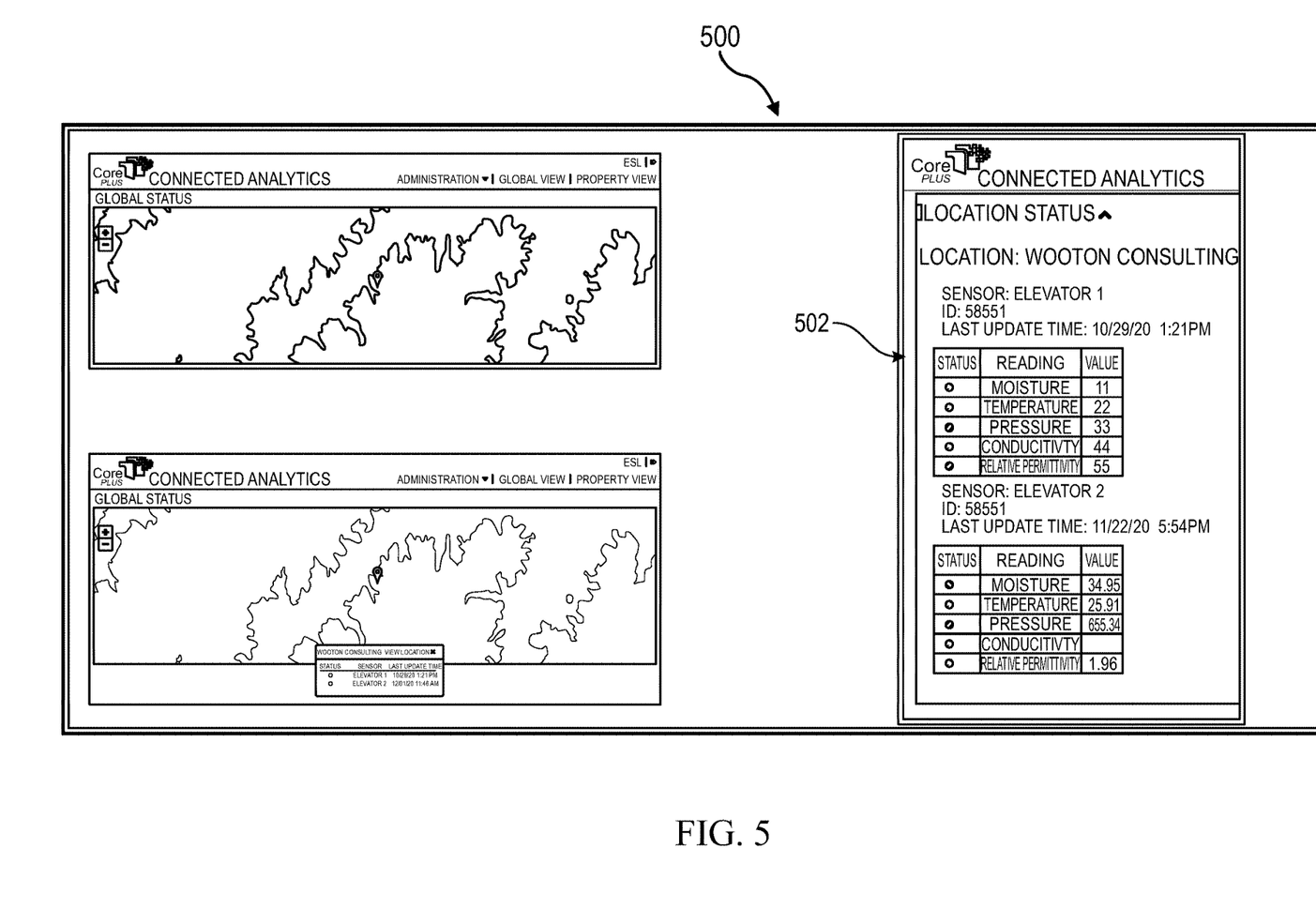
FIG. 5 is an illustration showing immediate access to fluid power system sensor details via the fluid power system dashboard, according to some embodiments.
Figure 6:
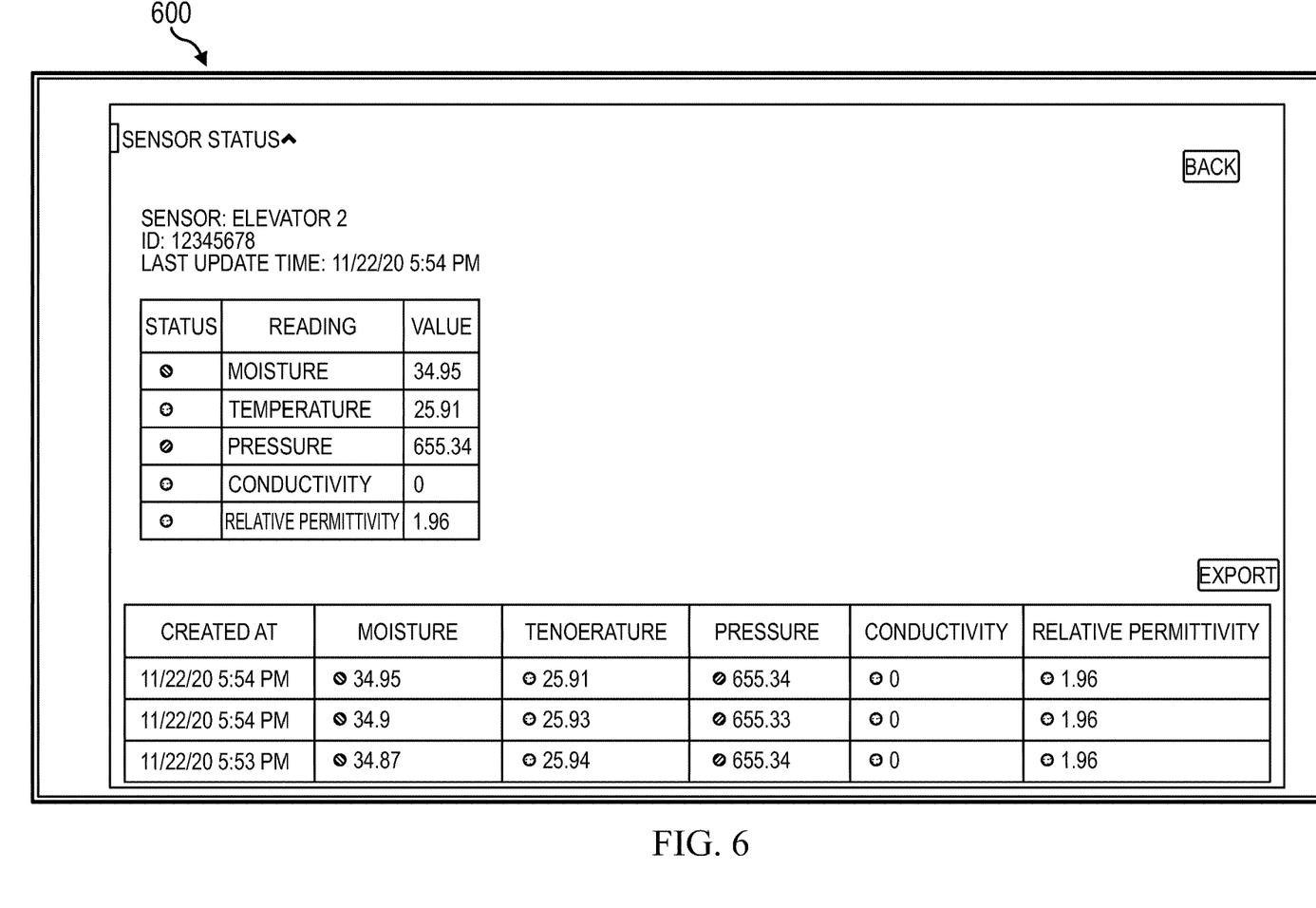
FIG. 6 is an illustration showing example fluid sensor status details for a fluid power system, according to some embodiments.

As noted, embodiments of the present systems and methods provide continuous monitoring to an unlimited audience. FIG. 4 is an illustration of (a screen shot of) global fluid power system dashboard 400, in accordance with various embodiments of the present systems and methods, such as may, by way of example, be provided by on user interface 135 of cloud monitoring system 130, or the like. FIG. 5 is an illustration (of a screen shot) showing immediate access 502 to fluid power system sensor details via fluid power system dashboard 500, such as may likewise be provided, by way of example, on user interface 135 of cloud monitoring system 130, or the like, in accordance with various embodiments of the present systems and methods. FIG. 6 is an illustration (of a screen shot) showing display of example fluid sensor status details 600 for a fluid power system (in this example, an elevator), including fluid moisture content, temperature, pressure, conductivity, and relative permittivity, such as may be displayed on fluid power system dashboard 400/500, via, by way of example, user interface 135 of cloud monitoring system 130, or the like, in accordance with various embodiments of the present systems and methods.

Figure 7:
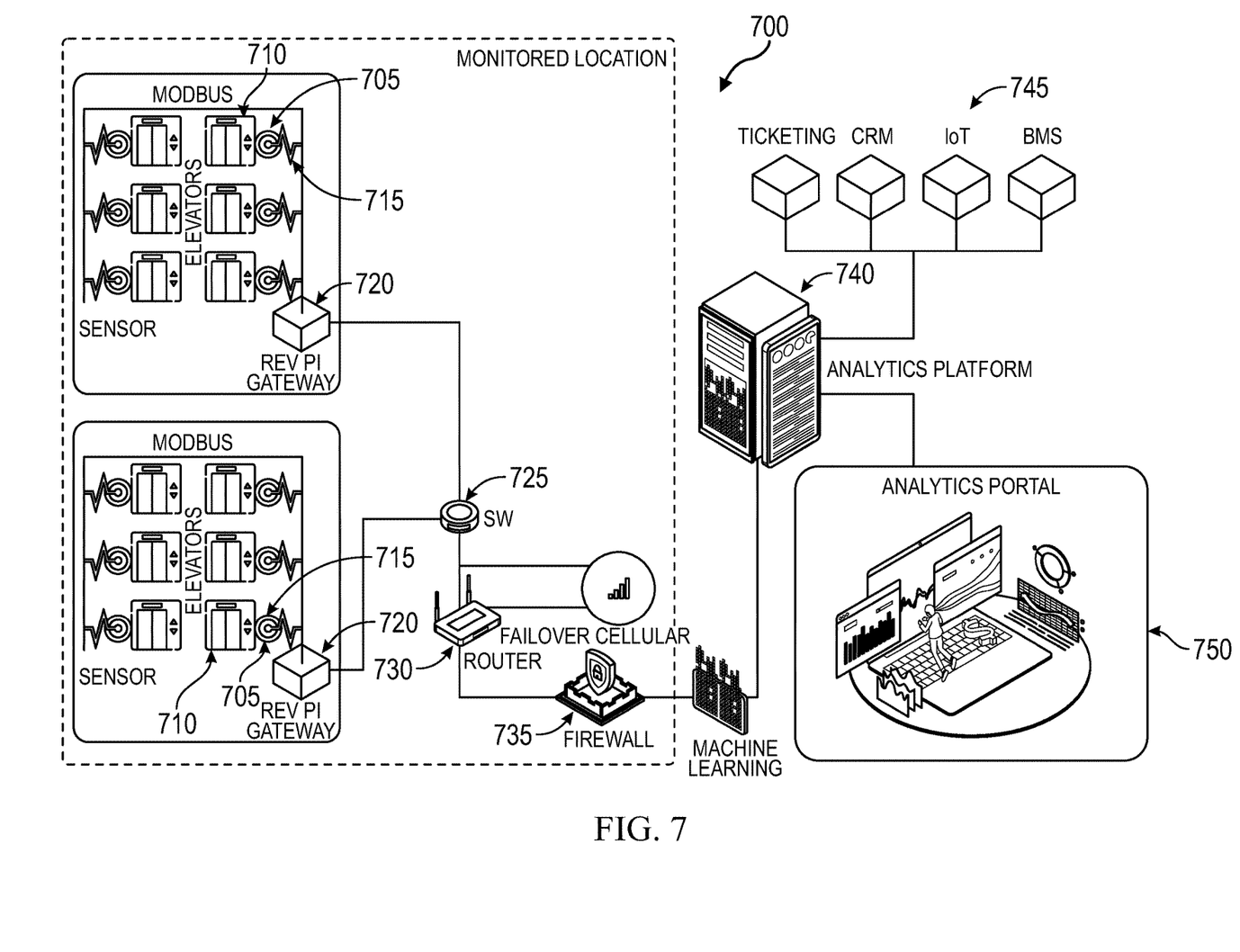
FIG. 7 is a block diagram of an example unified building (fluid power) management system and method architecture, according to some embodiments.

FIG. 7 is a block diagram of example unified building (fluid power) management system and method architecture 700, according to embodiments of the present fluid condition sensor systems and methods. FIG. 7 provides an overall system and method architecture, in accordance with carious embodiments, including, for example, sensor 705 (e.g., sensor(s) 105) placement(s) at each elevator 710 and network connectivity 715 to (local) centralized industrial IoT gateway 720 (e.g., 110). Data flows from the respective gateway through network switches 725, router 730, and firewall 735 via an encrypted channel to analytics platform 740 (e.g., 130). Analytics platform 740 provides integration into existing systems 745 and alerting and visibility through dashboard 750 (e.g., 135, 400, 500, etc.).

Embodiments of the present systems and methods support multiple fluid power system units. The present system units may each have the above-described power supply, connectivity to the cloud, gateway, sensor(s), etc., configured and tested, for installation in accordance with provided instructions. Component asset tracking may be provided via barcodes and label printing, to facilitate device management, and general automation. System maintenance may be provided, such as via "over the air" updates for sensors and gateways. These may include adding gateway algorithm features, improvements, error handling, etc. Security may be provided via data encryption, in transit and at rest, as well as via access authentication. This may include password and remote access management. Software architecture elements of the present systems match to the hardware selected for various implementations of the present systems, so as to provide an IoT sensor and gateway management platform, such as sensor payload processing, error handling, "over the air" update management from the cloud, and the like. This software flexibility facilitates integration with existing customer systems (fluid power systems), building management systems, third party solutions, and the like. This software flexibility can also be leveraged to provide customization of user workflows, role-based access, and the like.

Implementation of embodiments of the present systems and methods enables an executive, who, for example, overseas operations across multiple properties a consolidated view into fluid power system performance across each property and across multiple properties. Embodiments of the present systems and methods implement machine learning based scoring benchmarks to evaluate property safety in real time and recommend strategic actions that would improve property safety. Implementation of embodiments of the present systems and methods collect, measure, correlate and analyze data fluid power system data that impacts guest safety, employs machine learning based predictive recommendations to enhance guest safety and provides a unified view to monitor and enhance fluid power system safety, to a property manager, or the like, who, for example, oversees all operations of one or more properties.

As noted, in various embodiments, one or more of the techniques described herein may be performed by one or more computer systems. In other various embodiments, a tangible computer-readable storage medium may have program instructions stored thereon that, upon execution by one or more computer systems, cause the one or more computer systems to execute one or more operations disclosed herein. In yet other various embodiments, one or more systems may each include at least one processor and memory coupled to the processor(s), wherein the memory is configured to store program instructions executable by the processor(s) to cause the system(s) to execute one or more operations disclosed herein.

Thus, to implement various operations described herein, computer program code (i.e., instructions for carrying out these operations) may be written in any combination of one or more programming languages, including an object-oriented programming language such as Java, Smalltalk, Python, C++, or the like, conventional procedural programming languages, such as the "C" programming language or similar programming languages, or any of machine learning software. These program instructions may also be stored in a computer readable storage medium that can direct a computer system, other programmable data processing apparatus, controller, or other device to operate in a particular manner, such that the instructions stored in the computer readable medium produce an article of manufacture including instructions which implement the operations specified in the block diagram block or blocks. The program instructions may also be loaded onto a computer, other programmable data processing apparatus, controller, or other device to cause a series of operations to be performed on the computer, or other programmable apparatus or devices, to produce a computer implemented process such that the instructions upon execution provide processes for implementing the operations specified in the block diagram block or blocks.

It should be appreciated that the conception and specific embodiment disclosed may be readily utilized as a basis for modifying or designing other structures for carrying out the same purposes of the present invention. It is to be expressly understood, however, that each of the figures is provided for the purpose of illustration and description only and is not intended as a definition of the limits of the present invention.

The various operations described herein may be implemented in software executed by processing circuitry, hardware, or a combination thereof. The order in which each operation of a given method is performed may be changed, and various operations may be added, reordered, combined, omitted, modified, etc. It is intended that embodiment(s) described herein embrace all such modifications and changes and, accordingly, the above description should be regarded in an illustrative rather than a restrictive sense.

Various elements of the present fluid condition sensor and maintenance systems and methods may be implemented as modules. Modules may be implemented in hardware. In another embodiment, modules may be expressed in software executed by hardware. In still another embodiment, modules may be implemented in firmware operated by hardware. In still other embodiments, modules may be implemented in combinations of hardware, software, and/or firmware.

Modules implemented in software for execution by various types of processors may, for instance, include one or more physical or logical blocks of computer instructions, which may, for instance, be organized as an object or procedure. Nevertheless, the executables of an identified module need not be physically located together but may include disparate instructions stored in different locations which, when joined logically together, include the module and achieve the stated purpose for the module. Indeed, a module of executable code may be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices.

Reference is made herein to "configuring" a device or a device "configured to" perform some operation(s). It should be understood that this may include selecting predefined logic blocks and logically associating them. It may also include programming computer software-based logic of a retrofit control device, wiring discrete hardware components, or a combination of thereof. Such configured devices are physically designed to perform the specified operation (s).

Figure 8:
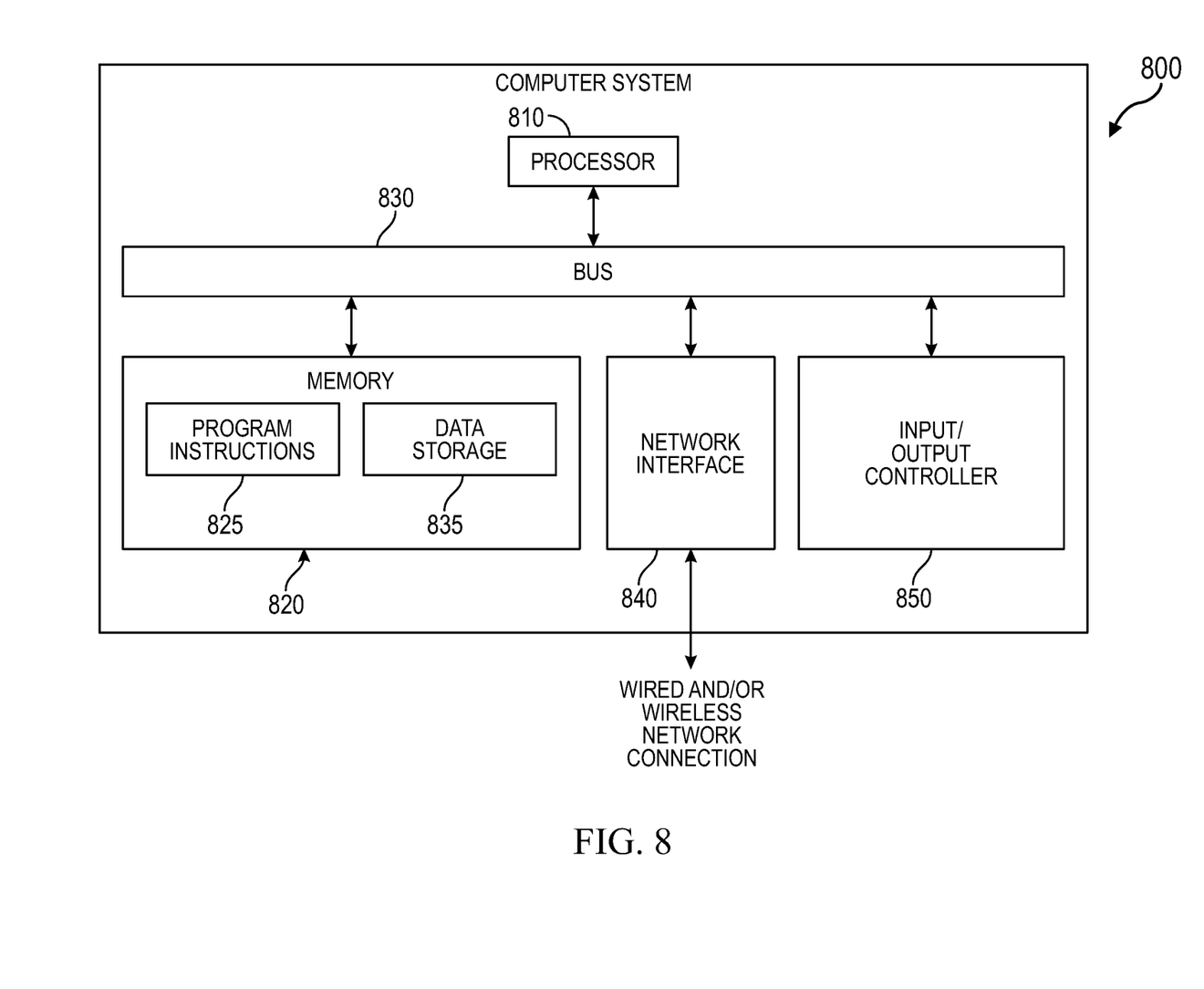
FIG. 8 is a block diagram depicting certain components of a computer system, device, station, or terminal configured to implement various techniques disclosed herein, according to some embodiments.

Embodiments of the present fluid condition sensor and maintenance systems and methods, as described herein, may be implemented at least in part as, or executed, at least in part, by one or more computer systems. One such computer system is illustrated in FIG. 8. In various embodiments, computer system 800 may be a single board computer, a server, a mainframe computer system, a workstation, a network computer, a desktop computer, a laptop, or the like. For example, in some cases, computer 800 may implement one or more steps of example processes 200 and/or 300 described above with respect to FIGS. 2 and 3, and/or a computer system such as computer system 800 may be used as part of, one or more of industrial IoT gateway 110, cloud monitoring system 130, etc. In various embodiments two or more of these computer systems may be configured to communicate with each other in any suitable way, such as, for example, via a public network, which may be the Internet, or the like, as discussed above, via a local area network using wired or wireless functionality, etc.

As illustrated, computer system 800 includes one or more processors 810 (and/or one or more processors having one or more processor cores, a processor with an integrated graphics processor, and/or the like) coupled to a system memory 820 via bus 830. Computer system 800 further includes a network interface 840 coupled to bus 830, and one or more I/O controllers 850, which in turn may provide optional connectivity for peripheral devices, such as for a cursor control device (mouse, trackball, or the like), keyboard, display(s), etc. Such I/O devices may be capable of communicating with I/O controller 850, for example, via a wired connection (e.g., serial port, Universal Serial Bus port) or wireless connection (e.g., Wi-Fi, Bluetooth, Near Field Communications Link, etc.). Other devices may include, for example, microphones, speakers, antennas/wireless transducers, etc.

In various embodiments, computer system 800 may be a single-processor system including one processor 810, or a multi-processor system including two or more processors 810, and/or or cores in one or more processors (e.g., two, four, eight, or another suitable number). Processor(s) 810 may be any processor capable of executing program instructions. For example, in various embodiments, processor(s) 810 may be general-purpose or embedded processors implementing any of a variety of instruction set architectures (ISAs), such as the x86, POWERPCR, ARMR, SPARCR, or MIPSR ISAs, or any other suitable ISA. In multi-processor systems, each of processor(s) 810 may commonly, but not necessarily, implement the same ISA. Also, in some embodiments, at least one processor 810 may be, or may include, a graphics processing unit (GPU) or another dedicated graphics-rendering device.

System memory 820 may be configured to store program instructions and/or data accessible by processor 810. In various embodiments, system memory 820 may be implemented using any suitable memory technology, such as static random-access memory (SRAM), synchronous dynamic RAM (SDRAM), nonvolatile/Flash-type memory, or any other type of memory. As illustrated, program instructions and data implementing certain operations and modules such as those described herein may be stored within system memory 820 as program instructions 825 and data storage 835, respectively. In other embodiments, program instructions and/or data may be received, sent, or stored upon different types of computer-accessible media or on similar media separate from system memory 820 or computer system 800.

A computer-accessible medium may include any tangible and/or non-transitory storage media or memory media such as electronic, magnetic, or optical media—e.g., disk or CD/DVD-ROM coupled to computer system 800 via bus 830. The terms "tangible" and "non-transitory," as used herein, are intended to describe a computer-readable storage medium (or "memory") excluding propagating electromagnetic signals, but are not intended to otherwise limit the type of physical computer-readable storage device that is encompassed by the phrase computer-readable medium or memory. For instance, the terms "non-transitory computer-readable medium" or "tangible memory" are intended to encompass types of storage devices that do not necessarily store information permanently, including for example, random access memory (RAM). Program instructions and data stored on a tangible computer-accessible storage medium in non-transitory form may further be transmitted by transmission media or signals such as electrical, electromagnetic, or digital signals, which may be conveyed via a communication medium such as a network and/or a wireless link.

In an embodiment, bus 830 may be configured to coordinate I/O traffic between processor 810, system memory 820, and any peripheral devices in the computer system, including network interface 840 or other peripheral interfaces. In some embodiments, bus 830 may perform any necessary protocol, timing, or other data transformations to convert data signals from one component (e.g., system memory 820) into a format suitable for use by another component (e.g., processor 810). In some embodiments, bus 830 may include support for devices attached through various types of peripheral buses, such as a variant of the Peripheral Component Interconnect (PCI) bus standard or the Universal Serial Bus (USB) standard, for example. In some embodiments, the function of bus 830 may be split into two or more separate components, such as a northbridge chipset and a southbridge chipset, for example. In addition, in some embodiments some or all the functionality of bus 830, such as an interface to system memory 820, may be incorporated directly into processor(s) 810.

Network interface 840 may be configured to allow data to be exchanged between computer system 800 and other devices attached to a network, such as other computer systems, or between nodes of computer system 800. In various embodiments, network interface 840 may support communication via wired or wireless general data networks, such as any suitable type of Ethernet network, for example; via telecommunications/telephony networks such as analog voice networks or digital fiber communications networks; via storage area networks such as Fibre Channel SANs, or via any other suitable type of network and/or protocol.

I/O controllers 850 may, in some embodiments, enable communications with one or more display terminals, keyboards, keypads, touchpads, scanning devices, voice or optical recognition devices, mobile devices, or any other devices suitable for entering or retrieving data by one or more computer system 800. Multiple I/O controllers 850 may be present in computer system 800 or may be distributed on various nodes of computer system 800. In some embodiments, I/O devices may be separate from computer system 800 and may interact with one or more nodes of computer system 800 through a wired or wireless connection, such as over network interface 840.

As shown in FIG. 8, system memory 820 may include program instructions 825, configured to implement certain embodiments described herein, and data storage 835, comprising various data may be accessible by program instructions 825. In an embodiment, program instructions 825 may include software elements, which may be configured to affect the operations discussed in FIGS. 1 through 7. Program instructions 825 may be implemented in various embodiments using any desired programming language, scripting language, or combination of programming languages and/or scripting languages (e.g., C, C++, C #, JAVA®, JAVASCRIPT®, PERL®, etc.). Data storage 835 may include data that may be used in these embodiments (e.g., recorded communications, profiles for different modes of operations, etc.). In other embodiments, other or different software elements and data may be included.

A person of ordinary skill in the art will appreciate that computer system 800 is merely illustrative and is not intended to limit the scope of the disclosure described herein. The computer system and devices may include any combination of hardware or software that can perform the indicated operations. In addition, the operations performed by the illustrated components may, in some embodiments, be performed by fewer components or distributed across additional components. Similarly, in other embodiments, the operations of some of the illustrated components may not be provided and/or other additional operations may be available. Accordingly, systems and methods described herein may be implemented or executed with other computer system configurations.

The various operations described herein, particularly in connection with FIGS. 2 and 3, may be implemented in software executed by processing circuitry, hardware, or a combination thereof. The order in which each operation of a given method is performed may be changed, and various operations may be added, reordered, combined, omitted, modified, etc. It is intended that embodiment(s) described herein embrace all such modifications and changes and, accordingly, the above description should be regarded in an illustrative rather than a restrictive sense.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A fluid condition sensor system, comprising:
one or more fluid condition sensors configured to monitor one or more operating parameters of fluid in a fluid power system; and
a gateway communicatively coupled to the one or more fluid condition sensors for communication of the one or more operating parameters of the fluid in the fluid power system via a data communications protocol interface, wherein the data communications protocol interface polls the one or more fluid condition sensors at a frequency that increases when non-nominal sensor readings are received, the gateway comprising:
a data communications protocol interface master function;
a cloud computing interface module; and
program instructions, that when executed by the gateway, causes the gateway to periodically sample fluid condition sensor readings via the data communications protocol interface, format the readings, and send the readings to a cloud computing message queuing telemetry transport broker for processing by a cloud monitoring system.

2. The system of claim 1, wherein the program instructions include machine learning employed to provide predictions of fluid quality.

3. The system of claim 2, wherein the predictions of fluid quality are used by the program instructions to create a work ticket related to the fluid power system.

4. The system of claim 1, wherein the program instructions include machine learning employed to provide predictions of buildup of varnish in the fluid power system.

5. The system of claim 4, wherein the predictions of buildup of varnish in the fluid power system are used by the program instructions to create a work ticket related to the fluid power system.

6. The system of claim 1, wherein a scoring algorithm applies machine learning to predict fluid power system failure.

7. The system of claim 6, wherein the program instructions are further executable to develop trend data to provide predictive analytics, wherein the predictive analytics use sensor readings over time to generate trend analytics data that feeds into a predictive data model, and the predictive data model determines a future state of a varnish level.

8. The system of claim 7, wherein the program instructions are further executable to provide preemptive alerts, via text messages, emails, an application program interface of a third-party system, and/or on a user interface of the cloud monitoring system, of the predictions of fluid quality, buildup of varnish in the fluid power system and/or fluid power system failure.

9. A fluid condition sensor method comprising:
monitoring, by one or more fluid condition sensors, one or more parameters of fluid in a fluid power system;
communicating the one or more parameters of the fluid in the fluid power system to a gateway via a data communications protocol interface, wherein the data communications protocol interface polls the one or more fluid condition sensors at a frequency that increases when non-nominal sensor readings are received;
employing, by the gateway, a data communications protocol interface master function, a cloud computing interface module, and program instructions to:
periodically sampling fluid condition sensor readings via the data communications protocol interface;

formatting the readings;
sending the readings to a cloud computing message queuing telemetry transport broker for processing by a cloud monitoring system.

10. The method of claim 9, wherein the program instructions include machine learning providing predictions of fluid quality.

11. The method of claim 10, further comprising the program instructions using the predictions of fluid quality to create a work ticket related to the fluid power system.

12. The method of claim 9, wherein the program instructions include machine learning providing predictions of buildup of varnish in the fluid power system.

13. The method of claim 12, further comprising the program instructions using the predictions of buildup of varnish in the fluid power system to create a work ticket related to the fluid power system.

14. The method of claim 9, further comprising applying, by a scoring algorithm, the machine learning to predict fluid power system failure.

15. The method of claim 14, wherein the program instructions are further executable to develop trend data to provide predictive analytics, wherein the predictive analytics use sensor readings over time to generate trend analytics data that feeds into a predictive data model, and the predictive data model determines a future state of a varnish level.

16. The method of claim 15, further comprising providing preemptive alerts, via text messages, emails, an application program interface of a third-party system, and/or on a user interface of the cloud monitoring system, of the predictions of fluid quality, buildup of varnish in the fluid power system and/or fluid power system failure.

17. A method for providing servicing for a fluid power system, comprising:
cleaning varnish off of surfaces in the fluid power system;
installing a fluid condition sensor system, comprising:
one or more fluid condition sensors monitoring one or more operating parameters of fluid in the fluid power system; and
an industrial internet of things a gateway communicatively coupled to the one or more fluid condition sensors, the industrial internet of things gateway communicating the one or more operating parameters of the fluid in the fluid power system, via a programmable logic controller data communications protocol interface, the industrial internet of things gateway comprising:
a programmable logic controller data communications protocol interface master function;
a cloud computing interface module; and
program instructions, that when executed by the industrial internet of things gateway, causes the industrial internet of things gateway to periodically sample fluid condition sensor readings via the programmable logic controller data communications protocol interface, format the readings, and send the readings to a cloud computing message queuing telemetry transport broker for processing by a cloud monitoring system;
issuing or obtaining a warranty, guarantee and/or service contract covering repair and/or replacement of named components that breakdown due to failure of the fluid power system;
providing, by the cloud monitoring system, monitoring of the one or more operating parameters of fluid in the fluid power system;
providing, by machine learning in the program instructions, predictions of fluid quality;
providing, by the machine learning, predictions of buildup of varnish in the fluid power system;
applying, by a scoring algorithm, machine learning to predict fluid power system failure; and
using the predictions of fluid quality, the predictions of buildup of varnish in the fluid power system and/or a prediction of fluid power system failure, by the program instructions, to create a work ticket related to the fluid power system.

18. The method of claim 17, further comprising polling, by the programmable logic controller data communications protocol interface, the connected one or more sensors at a frequency that increases as indication of non-nominal sensor readings are received and the program instructions are further executable to develop trend data to provide predictive analytics.

19. The method of claim 17, further comprising providing preemptive alerts, via text messages, emails, an application program interface of a third-party system, and/or on a user interface of the cloud monitoring system, of the predictions of fluid quality, buildup of varnish in the fluid power system and/or fluid power system failure.

20. The method of claim 17, further comprising financing one or more of the cleaning varnish off of surfaces in the fluid power system, installing the fluid condition sensor system, issuing or obtaining the warranty, guarantee and/or service contract, monitoring of the one or more operating parameters of fluid in the fluid power system, providing predictions of fluid quality and varnish in the fluid power system and predicting fluid power system failure.

\* \* \* \* \*